(12) United States Patent
Madjid et al.

(10) Patent No.: US 8,609,152 B2
(45) Date of Patent: Dec. 17, 2013

(54) COMPOSITIONS AND METHODS FOR EXTRACTING AND USING PHYTOCHEMICALS FOR THE TREATMENT OF INFLUENZA

(76) Inventors: Mohammad Madjid, Houston, TX (US); Harley R. Liker, Beverly Hills, CA (US)

( * ) Notice: Subject to any disclaimer, the term of this patent is extended or adjusted under 35 U.S.C. 154(b) by 685 days.

(21) Appl. No.: 12/730,119

(22) Filed: Mar. 23, 2010

(65) Prior Publication Data

US 2010/0298250 A1 Nov. 25, 2010

Related U.S. Application Data

(63) Continuation-in-part of application No. 12/564,878, filed on Sep. 22, 2009, which is a continuation of application No. 11/137,248, filed on May 24, 2005, now Pat. No. 7,611,738, application No. 12/730,119, which is a continuation-in-part of application No. 11/757,320, filed on Jun. 1, 2007, now abandoned.

(60) Provisional application No. 60/809,859, filed on Jun. 1, 2006.

(51) Int. Cl.
*A61K 36/00* (2006.01)

(52) U.S. Cl.
USPC .......................................................... 424/725

(58) Field of Classification Search
None
See application file for complete search history.

(56) References Cited

U.S. PATENT DOCUMENTS

| | | | |
|---|---|---|---|
| 5,411,733 A * | 5/1995 | Hozumi et al. ............... | 424/727 |
| 5,840,308 A | 11/1998 | Jassim et al. | |
| 5,891,440 A | 4/1999 | Lansky | |
| 5,902,616 A | 5/1999 | Hinnergardt et al. | |
| 5,989,557 A | 11/1999 | Bombardelli et al. | |
| 6,033,692 A | 3/2000 | Chukwu | |
| 6,060,063 A | 5/2000 | Lansky | |
| 6,312,753 B1 | 11/2001 | Kealey et al. | |
| 6,361,807 B1 | 3/2002 | Aviram et al. | |
| 6,375,993 B1 | 4/2002 | Aviram et al. | |
| 6,387,370 B1 | 5/2002 | Yegorova | |
| 6,387,418 B1 | 5/2002 | Aviram et al. | |
| 6,544,581 B1 | 4/2003 | Shrikhande et al. | |
| 6,641,850 B1 | 11/2003 | Aviram et al. | |
| 6,642,277 B1 | 11/2003 | Howard et al. | |
| 6,800,292 B1 | 10/2004 | Murad | |
| 6,855,352 B2 | 2/2005 | Shoji | |
| 2002/0012710 A1 | 1/2002 | Lansky | |
| 2002/0197341 A1 | 12/2002 | Lansky | |
| 2003/0134006 A1 | 7/2003 | Chukwu | |
| 2004/0009262 A1 | 1/2004 | Chukwu | |
| 2004/0126470 A1 | 7/2004 | Harpaz | |
| 2005/0118312 A1 | 6/2005 | Lansky | |
| 2006/0234934 A1 * | 10/2006 | Kilmon ........................... | 514/12 |
| 2007/0032558 A1 * | 2/2007 | Lerner et al. .................. | 514/743 |

FOREIGN PATENT DOCUMENTS

| | | |
|---|---|---|
| WO | 00/56177 | 0/2000 |
| WO | WO 0137848 | 5/2001 |
| WO | WO 02/094303 A1 | 11/2002 |
| WO | 2006/127832 | 11/2006 |
| WO | 07/127263 | 8/2007 |

OTHER PUBLICATIONS

Malik Arshi et al. "Pomegrante fruit juice for chemoprevention and chemotherapy of prostate cancer," Proceedings of the National Academy of Sciences of USA, vol. 102, No. 41, Oct. 11, 2005, pp. 14813-14818.
Aviram et al. "Pomegranate juice consumption reduces oxidative stress, atherogenic modifications to LDL, and platelet aggregation: Studies in humans and in atherosclerotic apolipoprotein E-deficient mice," American Journal of Clinical Nutrition 200005 US, vol. 71, No. 5, May 2000, pp. 1062-1076.
Malik Arshi et al. "Prostate cancer prevention through pomegranate fruit," Cell Cycle, Feb. 2006, vol. 5, No. 4, Feb. 2006, pp. 371-373.
Pantuck A. J. et al. "831, Phase II study of pomegranate juice for men with rising PSA following surgery of radatien for prostate cancer," Journal of Urology, Lippincott Williams & Wilkins, Baltimore, MD, US, vol. 17, No. 4, Suppl. S, Apr. 1, 2005, pp. 225-226.
Kim Nam Deuk et al. "Chemopreventive and adjuvant therapeutic potential of pomegranate (*Punica granatum*) for human breast cancer," Breast Cancer Research and Treatment, vol. 71, No. 3, Feb. 2002, pp. 203-217.

(Continued)

*Primary Examiner* — Terry A McKelvey
*Assistant Examiner* — Randall Winston
(74) *Attorney, Agent, or Firm* — Cotman IP Law Group, PLC; Obi Iloputaife

(57) ABSTRACT

Methods and compositions for treating at least one symptom of a viral infection, said method of treatment comprising administering to a subject with a least one symptom of a viral infection an effective dosage unit of a composition comprising pomegranate extract. The compositions comprise pomegranate extract comprising polyphenols. The composition is produced by a process comprising providing one or more pomegranate solids selected from the group consisting of a pericarp, inner membrane and seeds, creating a mixture comprising said one or more pomegranate solids in an aqueous solution, heating said mixture to a temperature that permits enzyme catalysis of said pomegranate solids, and removing residual insoluble solid materials from said mixture to provide said pomegranate extract. Compositions containing the extract may be used as a food product, beverage, pharmaceutical preparations, nutritional supplements, vitamin supplements, food additives, and food supplements.

15 Claims, 1 Drawing Sheet

(56) References Cited

OTHER PUBLICATIONS

Pantuck A J. eta I. "Phase II study of pomegranate juice for men with rising prostate-specific antigen following surgery of radiation for prostate cancer," Clinical Cancer Research 20060701, vol. 12, No. 13, Jul. 1 2006, pp. 4018-4026.

Supplementary European Search Report for EP Application No. EP 07 75 8647, mailed on Jan. 29, 2010, 9 pages.

Albrecht, et al., "Pomegranate Extracts Potently Suppress Proliferation, Xenograft Growth, and Invasion of Human Prostate Cancer Cells," European Urology Supplements, vol. 2, Issue 6, 24-27 p. 138 (Sep. 2003).

Seeram, et al., "In vitro antiproliferative, apoptotic and antioxidant activities of punicalagin, ellagic acid and a total pomegranate tannin extract are enhanced in combination with other polyphenols as found in pomegranate juice," Journal of Nutritional Biochemistry, 16(6) pp. 360-367 (2005).

DW ACC 2003103614, Dec. 3, 2002, Lansky.

Seeram et al. "Bioavailability of ellagic acid in human plasma after consumption of ellagitannins from pomegranate (*Punica granatum* L.) juice", Clinica Chimica Acta 348 (2004) 63-68.

Seeram, et al., "Pomegranate Juice Ellagitannin Metabolites Are Present in Human Plasma and Some Persist in Urine for Up to 48 Hours", Journal of Nutrition, 2006, 2481-2485.

Seeram, et al. "Pomegranate Juice and Extracts Provide Similar Levels of Plasma and Urinary Ellagitannin Metabolites in Human Subjects" Journal of Medicinal Food, 11 (2) 2008, 390-394.

D. Syed, et al. "Photochemopreventive Effect of Pomegranate Fruit Extract on UVA-mediated Activation of Cellular Pathways in Normal Human Epidermal Keratinocytes" Photochemistry and Photobiology, 2006, 82: 398-405.

Adams, et al. "Pomegranate Juice, Total Pomegranate Ellagitannins, and Punicalagin Suppress Inflammatory Cell Signaling in Colon Cancer Cells" Journal of Agricultural and Food Chemistry, 2006, 54, 980-985.

V. Adhami, et al. "Polyphenols from green tea and pomegranate for prevention of prostate cancer" Free Radical Research, Oct. 2006; 40(10): 1095-1104.

S. Kasimsetty, et al. "Effects of Pomegranate Chemical Constituents/Intestinal Microbial Metabolites on CYP1B1 in 22Rv1 Prostate Cancer Cells" Journal of Agriculture and Food Chemistry, 2009, 57, 10636-10644.

Sartippour, et al., "Ellagitannin-rich pomegranate extract inhibits angiogenesis in prostate cancer in vitro and in vivo" International Journal of Oncology, 2008, 32:475-480.

Rettig, et al. "Pomegranate extract inhibits androgen-independent prostate cancer growth through a nuclear factor-KB-dependent mechanism" Molecular Cancer Therapy, 2008; 7(9): 2662-71.

Seeram, et al."Pomegranate Ellagitannin-Derived Metabolites Inhibit Prostate Cancer Growth and Localize to the Mouse Prostate Gland" Journal of Agricultural and Food Chemistry, 2007, 55, 7732-7737.

Hong, et al. "Pomegranate polyphenols down-regulate expression of androgen-synthesizing genes in human prostate cancer cells overexpressing the androgen receptor" Journal of Nutritional Biochemistry, 2008, 8 pages.

J. Trombold, et al. "Ellagitannin Consumption Improves Strength Recovery 2-3 d after Eccentric Exercise" The American College of Sports Medicine, 2010, 493-498.

B. Fuhrman, et al. "Pomegranate juice polyphenols increase recombinant paraoxonase-1 binding to high-density lipoprotein: Studies in vitro and in diabetic patients" Nutrition 26 (2010) 359-366.

J. Khateeb, et al. "Paraoxonase 1 (PON1) expression in hepatocytes is upregulated by pomegranate polyphenols: A role for PPAR" Atherosclerosis, 2009, 7 pages.

M. Davidson, et al. "Effects of Consumption of Pomegranate Juice on Carotid Intima-Media Thickness in Men and Women at Moderate Risk for Coronary Heart Disease" American Journal of Cardiology, 2009, 936-942.

O. Rozenberg, et al. Pomegranate juice sugar fraction reduces macrophage oxidative state, whereas white grape juice sugar fraction increases it Atherosclerosis, 188 (2006) 68-76.

Mattiello, et al. "Effects of Pomegranate Juice and Extract Polyphenols on Platelet Function" Journal of Medicinal Food, 12 (2) 2009, 7 pages.

Sumner, et al. "Effects of Pomegranate Juice Consumption on Myocardial Perfusion in Patients With Coronary Heart Disease" American Journal of Cardiology, 2005, 5 pages.

M. Aviram, et al. "Pomegranate juice consumption inhibits serum angiotensin converting enzyme activity and reduces systolic blood pressure" Atherosclerosis, 158 (2001) 195-198.

M. Aviram, et al. "Pomegranate Phenolics from the Peels, Arils, and Flowers Are Antiatherogenic: Studies in Vivo in Atherosclerotic Apolipoprotein E-Deficient (E0) Mice and in Vitro in Cultured Macrophages and Lipoproteins" Journal of Agricultural and Food Chemistry, 2008, 56, 1148-1157.

Shiner et al. "Macrophage paraoxonase 2 (PON2) expression is up-regulated by pomegranate juice phenolic anti-oxidants via PPAR and AP-1 pathway activation" Atherosclerosis, 2007, 9 pages.

de Nigris, et al. "Effects of a Pomegranate Fruit Extract rich in punicalagin on oxidation-sensitive genes and eNOS activity at sites of perturbed shear stress and atherogenesis" Cardiovascular Research, 2007, 73, 414-423.

de Nigris, et al."Pomegranate juice reduces oxidized low-density lipoprotein downregulation of endothelial nitric oxide synthase in human coronary endothelial cells" Nitric oxide, 2006 15 259-263.

L. Ignarro, et al. "Pomegranate juice protects nitric oxide against oxidative destruction and enhances the biological actions of nitric oxide" Nitric oxide, 2006, 15, 93-102.

de Nigris et al. "Beneficial effects of pomegranate juice on oxidation-sensitive genes and endothelial nitric oxide synthase activity at sites of perturbed shear stress" Proceedings of the National Academy of Sciences, 2005, vol. 102, No. 13, 6 pages.

Rosenblat, et al. "Pomegranate Byproduct Administration to Apolipoprotein E-Deficient Mice Attenuates Atherosclerosis Development as a Result of Decreased Macrophage Oxidative Stress and Reduced Cellular Uptake of Oxidized Low-Density Lipoprotein" Journal of Agricultural and Food Chemistry, 2006, 54, 1928-1935.

de Nigris, et al. "The influence of pomegranate fruit extract in comparison to regular pomegranate juice and seed oil on nitric oxide and arterial function in obese Zucker rats" Nitric Oxide, 2007 17, 50-54.

Kaplan, et al. "Pomegranate Juice Supplementation to Atherosclerotic Mice Reduces Macrophage Lipid Peroxidation, Cellular Cholesterol Accumulation and Development of Atherosclerosis" Journal of Nutrition, 2001, 2082-2089.

M. Abu Zaid, et al. "Inhibition of UVB-mediated Oxidative Stress and Markers of Photoaging in Immortalized HaCaT Keratinocytes by Pomegranate Polyphenol Extract POMx" Photochemistry and Photobiology, 2007, 83: 882-888.

Lorean et al. "Maternal Dietary Supplementation with Pomegranate Juice Is Neuroprotective in an Animal Model of Neonatal Hypoxic-Ischemic Brain Injury" Pediatric Research, 2005, vol. 57, No. 6, 7 pages.

Shah, et al. "Pomegranate juice decreases amyloid load and improves behavior in a mouse model of Alzheimer's disease" Neurobiology of Disease, 2006, Abstract.

D. Bialonska, et al. "Urolithins, Intestinal Microbial Metabolites of Pomegranate Ellagitannins, Exhibit Potent Antioxidant Activity in a Cell-Based Assay" Journal of Agriculture and Food Chemistry, 2009, 57, 10181-10186.

Y. Zhang, et al. "Absence of Pomegranate Ellagitannins in the Majority of Commercial Pomegranate Extracts: Implications for Standardization and Quality Control" Journal of Agricultural and Food Chemistry, 2009, 57, 7395-7400.

Y. Zhang, et al. "International Multidimensional Authenticity Specification (IMAS) Algorithm for Detection of Commercial Pomegranate Juice Adulteration", Journal of Agricultural and Food Chemistry, 2009, 9 pages.

S. Madrigal-Carballo, et al. "Pomegranate (*Punica granatum*) supplements: authenticity, antioxidant and polyphenol composition" Journal of Functional Foods, 2009, 6 pages.

(56) References Cited

OTHER PUBLICATIONS

K. Martin et al. "Development of a novel pomegranate standard and new method for the quantitative measurement of pomegranate polyphenols" Journal of Science of Food and Agriculture, 2009; 89:157-162.

N. Seeram, et al. "Comparison of Antioxidant Potency of Commonly Consumed Polyphenol-Rich Beverages in the United States" Journal of Agricultural and Food Chemistry, 2008, 56, 1415-1422.

Rosenblat, et al. "Consumption of polyphenolic-rich beverages (mostly pomegranate and black currant juices) by healthy subjects for a short term increased serum antioxidant status, and the serum's ability to attenuate macrophage cholesterol accumulation" Food & Function, 2010, 1, 99-109.

G. Borges, et al. "Comparison of the polyphenolic composition and antioxidant activity of European commercial fruit juices" Food & Function, 2010, 11 pages.

D. Bialonska, et al. "The Effect of Pomegranate (*Punica granatum* L.) Byproducts and Ellagitannins on the Growth of Human Gut Bacteria" Journal of Agriculture and Food Chemistry, 2009, 57, 8344-8349.

A. Sundararajana, et al. "Influenza virus variation in susceptibility to inactivation by pomegranate polyphenols is determined by envelope glycoproteins" Elsevier, 2010 (1-9).

R. Oliveira, et al. "Effects of feeding polyphenols from pomegranate extract on health, growth, nutrient digestion, and immunocompetence of calves" American Dairy Science Association, 2010, 93:4280-4291.

M. Haidari, et al. "Pomegranate(*Punicagranatum*) purified polyphenol extract inhibits influenza virus and has a synergistic effect with oseltamivir" Phytomedicine, 2009, 10 pages.

D. Bialonska, et al. "The influence of pomegranate by-product and punicalagins on selected groups of human intestinal microbiota" International Journal of Food Microbiology, 140 (2010) 175-182.

M. Reddy, et al. "Antioxidant, Antimalarial and Antimicrobial Activities of Tannin-Rich Fractions, Ellagitannins and Phenolic Acids from *Punica granatum* L." Planta Medica, 2007, 7 pages.

M. Shukla, et al. "Consumption of hydrolyzable tannins-rich pomegranate extract suppresses inflammation and joint damage in rheumatoid arthritis" Nutrition, 24, 2008, 733-743.

Z. Rasheed, et al. "Polyphenol-rich pomegranate fruit extract (POMx) suppresses PMACI-induced expression of pro-inflammatory cytokines by inhibiting the activation of MAP Kinases and NF-κB in human KU812 cells" Journal of Inflammation, 2009, 12 pgs.

Glycaemic Index Research Service "A Study to Measure the Glycaemic Index Value of Pomegranate Juice" The School of Molecular and Microbial Bio-sciences at Sydney University, Mar. 2009, 22 pgs.

B. McFarlin, et al. "Pomegranate seed oil consumption during a period of high-fat feeding reduces weight gain and reduces type 2 diabetes risk in CD-1 mice" British Journal of Nutrition, 2008, 6 pages.

W. Rock, et al. "Consumption of Wonderful Variety Pomegranate Juice and Extract by Diabetic Patients Increases Paraoxonase 1 Association with High-Density Lipoprotein and Stimulates Its Catalytic Activities" Journal of Agricultural and Food Chemistry, 2008, 56, 8704-8713.

M. Rosenblat, et al. "Anti-oxidative effects of pomegranate juice (PJ) consumption by diabetic patients on serum and on macrophages" Atherosclerosis, 187 (2006) 363-371.

Q. Zhang, et al. "Dietary antioxidants improve arteriogenic erectile dysfunction" International Journal of Andrology, 33, 2010, 1-11.

K. Azadzoi, et al."Oxidative Stress in Arteriogenic Erectile Dysfunction: Prophylactic Role of Antioxidants" Journal of Urology, 2005, vol. 174, 386-393.

Forest, et al. "Efficacy and safety of pomegranate juice on improvement of erectile dysfunction in male patients with mild to moderate erectile dysfunction: a randomized, placebo-controlled, double-blind, crossover study" International Journal of Impotence Research, 2007, 1-4.

S. Strum, et al. "Pomegranates and Prostate Health: A Research Report", PCRI Insights, 2008, vol. 11: No. 3, 36 pages.

A. McCutcheon, et al. "Scientific and Clinical Monograph for POM Wonderful Pomegranate Juice" American Botanical Council, 2008, 20 pgs.

M. Aviram, et al. "Pomegranate juice flavonoids inhibit low-density lipoprotein oxidation and cardiovascular diseases: Studies in atherosclerotic mice and in humans" Drugs Under Experimental and Clinical Research XXVIII, 2003, 15 pages.

M. Warren, et al. "Pomegranate's Ancient Roots to Modern Medicine, Pomegranates: Ancient Roots to Modern Medicine" Taylor and Francis, 2006, 158-166.

D. Heber, et al. "Safety and Antioxidant Activity of a Pomegranate Ellagitannin-Enriched Polyphenol Dietary Supplement in Overweight Individuals with Increased Waist Size" Journal of Agricultural and Food Chemistry, 2007, 55, 10050-10054.

D. Farkas, et al. "Pomegranate Juice Does Not Impair Clearance of Oral or Intravenous Midazolam, a Probe for Cytochrome P450-3A Activity: Comparison With Grapefruit Juice" Journal of Clinical Pharmacology, 2007; 47;286-294.

F. Afaq, et al. "Protective effect of pomegranate-derived products on UVB-mediated damage in human reconstituted skin" Experimental Dermatology, 2009.

M. Abu Zaid, et al. "Inhibition of UVB-mediated Oxidative Stress and Markers of Photoaging in Immortalized HaCaT Keratinocytes by Pomegranate Polyphenol Extract POMx" Photochemistry and Photobiology, 2007.

D Pérez et al., Wine, Diet, Antioxidant Defenses and Oxidative Damage. Annals of the New York Academy of Sciences (2002),957:136-145.

KJ Joshipura, et al., The Effect of Fruit and Vegetable Intake on Risk for Coronary Heart Disease. Annals of Internal Medicine (2001),134:1106-1114.

http://www.wonderfulpomegranateresearch.com/featured May 2010.

* cited by examiner

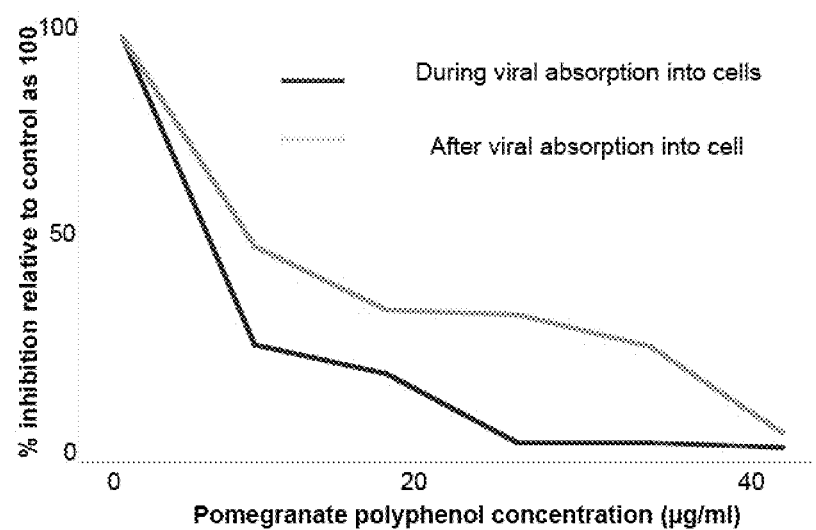

COMPOSITIONS AND METHODS FOR EXTRACTING AND USING PHYTOCHEMICALS FOR THE TREATMENT OF INFLUENZA

CROSS REFERENCE TO RELATED APPLICATIONS

This application is a continuation-in-part of prior-filed and co-pending U.S. patent application Ser. No. 12/564,878 entitled PROCESS FOR EXTRACTING PHYTOCHEMICALS FROM POMEGRANATE SOLIDS AND COMPOSITIONS AND METHODS OF USE THEREOF, filed Sep. 22, 2009, which is a continuation of U.S. patent application Ser. No. 11/137,248, filed May 24, 2005, (now U.S. Pat. No. 7,611,738), and this application is also a continuation-in-part of prior-filed and U.S. patent application Ser. No. 11/757,320 entitled METHOD OF USING COMPOSITION COMPRISING POMEGRANATE EXTRACTS AGAINST INFLUENZA, filed Jun. 1, 2007 now abandoned, which claims benefit to U.S. Provisional Patent Application Ser. No. 60/809,859, filed Jun. 1, 2006, all of the above which are hereby incorporated by reference in their entirety.

BACKGROUND OF THE INVENTION

1. Field of the Invention

The present invention relates generally to pomegranate extracts, and more particularly, to compositions and methods for extracting and using phytochemicals for the treatment of influenza.

2. Description of the Related Art

It is well-known that fruits and vegetables are an essential part of a healthy diet. Chief, among the reasons, is that fruits and vegetables are rich sources of important phytochemicals, which provide essential nutrients and enhance the body's ability to prevent and fight disease. There is a multitude of phytochemicals, in unique combinations, in different fruits and vegetables, and each functions differently in the body: as anti-oxidants, as anti-allergenic, as anti-carcinogenic, as anti-inflammatory, as anti-viral, and/or anti-proliferative.

The pomegranate has recently been acclaimed for its health benefits and for its disease-fighting antioxidant potential. Antioxidants are important because they are believed to protect the body against free radicals, the harmful molecules that can cause heart disease, premature aging, Alzheimer's disease, blindness, and a variety of cancers.

Studies have shown that pomegranate juice has more polyphenol antioxidants than any other drink, such as red wine, green tea, blueberry juice, cranberry juice and orange juice. Currently, the two common ways of consuming pomegranates are by eating the fleshy arils of the pomegranate and by drinking the juice obtained from the arils.

There are many kinds of antioxidants, some produced by the body and others derived from the foods we eat. When the body's natural antioxidant defenses are lowered, or greater amounts of free radicals are being produced, the body becomes more dependent upon food sources of antioxidants.

The importance of influenza viruses as worldwide pathogens for humans and domestic animals is well recognized. Influenza is a major cause of morbidity and death. According to the Office of Technology Assessment of the US Congress, each year, in the United States alone, "the flu" accounts for 110,000 hospitalizations, 1 to 3 billion dollars in direct costs, and 10 to 15 billion dollars in indirect costs. Influenza has been established as a serious human affliction that can cause localized epidemics and global pandemic of acute respiratory infection. There is a growing concern for potential pandemic outbreak of influenza virus from the strain currently in birds in Asia or another influenza virus.

Avian influenza is caused by type A strains of influenza virus. Avian influenza occurs throughout the world. Infected birds may display a wide range of symptoms, from a mild illness to a highly contagious fatal disease. The highly contagious disease is caused by an especially virulent strain of influenza virus. Infection by this strain is associated with a sudden onset of severe symptoms, such as a lack of energy, decreased egg production, soft shelled eggs, a swelling of the head, eyelids, etc., nasal discharge, coughing or diarrhea, resulting in death. At present, 15 subtypes have been identified that can infect birds but only H7, H5 and H9 subtypes are associated with outbreaks. The current Asian and British Columbia outbreaks are caused by a H5N1 and H7N3 strains, respectively. As discussed above, influenza viruses are a public health concern because these viruses lack a mechanism for proofreading nucleic acid replication as well as a repair system for correcting such errors. Thus, influenza viruses are especially prone to a high mutation rate during transcription. Additionally, influenza viruses are able to exchange or swap genetic material from other subtypes from different species, thus allowing subtypes to cross the species barrier that normally prevents the cross infection of species specific viruses from one species to another unrelated species. This species barrier normally prevents avian influenza virus strains from infecting humans, but occasionally new strains may have genetic material from both avian and human influenza virus strains. This exchange of genetic material occurs when there is a close proximity between humans and domestic poultry and swine. Swine may act as a reservoir for both human and avian strains. Thus swine act as a natural incubator for the emergence of new strains that can infect humans as well as avian species.

As mentioned above, influenza is prone to minor changes though genetic material to one or more of the major surface antigens during replication. The so-called antigenic drift is responsible for the seasonal epidemics because it can enable the virus to infect persons with only partial immunity from a prior exposure to the virus. Influenza A viruses are especially prone to antigenic drift. Major changes in the H and N antigens result in antigenic shift. Antigenic shift results in a new viral subtype and it can cause major epidemics and pandemics due to minimal immunity in population. Pandemics happen when a novel influenza virus emerges that infects and can be efficiently transmitted between humans. Hence, there is a need for a composition that provides for one or more anti-viral mechanisms that are not affected by antigenic drift.

Influenza viral infection may be associated with redox changes characteristic of oxidative stress. A more oxidized environment may favor further viral infection and stimulates viral protein synthesis. Various studies suggest that apoptosis of mammalian cells may be caused by alteration of intracellular redox condition induced by influenza virus infection. It was recently reported that certain antioxidants inhibited the growth of influenza viruses in Madin-Darby canine kidney (MDCK) cells and in another study, antioxidants inhibited the replication of viral strains in peripheral blood lymphocytes. These substances have proven useful in the field treating various illnesses; however there has not been any progress in the creation of a prophylactic method for use with antioxidant compounds. This lack of effect by other antioxidants on viral titer might represent the difference in biological availability of these compounds or that anti-viral activity operates through mechanisms other than anti-oxidation. Therefore, there exists a need in the field to provide a prophylactic method for the reduction of the incidence of contracting an illness caused by influenza virus.

BRIEF SUMMARY OF THE PREFERRED EMBODIMENTS

Methods are provided for producing an extract containing phytochemicals from pomegranate solids. The pomegranate solids are anyone or more of the group consisting of the pericarp, inner membrane and seeds. The extract produced differs from commercially-available pomegranate juice in that the extract is substantially derived from the pomegranate solids, whereas pomegranate juice is substantially derived from the sweet, fleshy arils.

In one preferred embodiment, the method includes the following steps. Anyone or a combination of the pericarp, inner membrane and seeds are selected and a mixture is formed comprising the pomegranate solids and an aqueous solution. The mixture is then heated to about 60° F. to 210° F., preferably of about 85° F. to 185° F. and optimally of about 110° F. to 160° F. Enzymes are added to the mixture in an amount sufficient to at least partially degrade the pomegranate solids and liberate phytochemicals from the plant. tissues and/or cells. Once liberated, the phytochemicals may react and/or polymerize to create new phytochemical compounds or reaction products. The residual insoluble solid materials are removed from the mixture to provide an extract containing phytochemicals.

In another preferred embodiment, extracts containing phytochemicals from a pomegranate are provided. Such extracts are characterized by a significantly higher total polyphenol content, particularly of the high molecular weight polyphenol (e.g., punicalagin), than is found in pomegranate juice. Such extracts may be obtained from the methods disclosed herein.

In a further preferred embodiment, food products and beverages are provided comprising the extract containing phytochemicals from a pomegranate.

In yet a further preferred embodiment, compositions comprising the extract containing phytochemicals from a pomegranate are provided. Such compositions may be in form of tablets, suspensions, implants, solutions, emulsions, capsules, powders, syrups, liquid compositions, ointments, lotions, creams, pastes, and gels. Such compositions may also be in form of pharmaceutical preparations, nutritional supplements, vitamin supplements, food additives, and food supplements.

In a further preferred embodiment, compositions containing the extract and the pomegranate juice are provided. The combination of the extract and pomegranate juice not only produces a composition having a higher total polyphenol content, as compared to the pomegranate juice alone, but it also provides the broad spectrum of the different polyphenols which predominate the pomegranate juice and extract.

It is further an object of certain embodiments of the invention to provide a method for reducing the incidence of contracting an illness caused by influenza viruses.

In the first aspect, the present invention relates to a method for the prophylactic use of an anti-viral composition to reduce the incidence of contracting an illness. The method comprises the steps of administering to a subject that has been, or will be, exposed to an illness caused by an influenza virus, an amount of an anti-viral composition having a composition extracted from fruits of pomegranate; and optionally an acceptable carrier. The amount of anti-viral composition is effective, when administered, to reduce the incidence of contracting the illness.

In a second aspect of the invention, a prophylactic anti-viral composition having ingredients obtainable from pomegranate fruit is disclosed. The anti-viral composition is effective, when administered as a nasal spray or as an inhalant spray to a subject that has been, or will be, exposed to an illness caused by influenza virus, to reduce the incidence of contracting said illness.

These and various other advantages and features of novelty that characterize the invention are pointed out with particularity in the claims annexed hereto and forming a part hereof. However, for a better understanding of the invention, its advantages, and the objects obtained by its use, reference should be made to the accompanying descriptive matter, in which there is described a preferred embodiment of the invention.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications and equivalents thereof.

BRIEF DESCRIPTION OF THE DRAWINGS

The above and other aspects, features and advantages of the invention will be more apparent from the following more particular description thereof, presented in conjunction with the following drawings wherein:

FIG. 1 is illustrates inhibition of viral replication by PJ after and during viral absorption into cells.

DETAILED DESCRIPTION OF THE PREFERRED EMBODIMENTS

As used herein, the term "phytochemicals" refers collectively to compounds which are naturally-occurring in the pomegranate and to reaction products and metabolites of these compounds, which are considered to have a beneficial effect on the human health. Examples of such phytochemicals include, but are not limited to polyphenols, estrogens and phytoestrogens.

As used herein, the term "polyphenols" refers generally to a family of naturally-occurring compounds in the pomegranate and includes phenols and polyphenols. Phenols are a class of chemical compounds consisting of a single phenol unit in their structure. Although similar to alcohols, phenols have unique properties including relatively higher acidities due to the aromatic ring tightly coupled to the oxygen and a relatively loose bond between the oxygen and the hydrogen. Examples of phenolic compounds within this group include ellagic acid and gallic acid. Polyphenols are a group of compounds, characterized by the presence of more than one phenolic group. Polyphenols include tannins (e.g., ellagitannins and gallotannins), flavonoids (e.g., anthocyanins and isoflavones) and stilbenes (e.g., resveratrol).

As used herein, the term "pomegranate juice" refers to the juice that is substantially obtained from the arils of the pomegranate.

As used herein, the term "pomegranate solids" refers to anyone or a combination of the pericarp, the inner membrane and seeds of a pomegranate.

It has been surprisingly discovered that extracts obtained from the pomegranate solids, in accordance with the methods disclosed herein, have a substantially higher total polyphenol content than is found in the juice from the pomegranate arils. This is particularly true with respect to the higher molecular weight polyphenols and, in particular, punicalagin.

Punicalagin is a powerful antioxidant, protecting cardiovascular function and accurate cellular replication. Thus, punicalagin is responsible, in part, for the high antioxidant activity of the extract. While the antioxidant and other beneficial health effects of the extract are due to the presence of polyphenols, the presence of other phytochemical compounds in the extract, or the synergistic effect of these phytochemicals, may also be responsible for the anti-oxidant and other beneficial health effects of the extract.

In addition to punicalagin, other high molecular weight polyphenols have been characterized in the extract of pomegranate solids. These high molecular weight polyphenols include ellagitannin and other hydrolysable tannins, such as punicacortein A, punicalin, pedunculagin, and gallotanin dimmers and trimers.

Moreover, a large number of anthocyanins have been characterized in the extract of the pomegranate solids. Examples of the anthocyanins include pelargonidin 3-glucoside, cyaniding 3-glucoside, delphinidin 3-glucoside, pelargonidin 3,5-diglucoside, cyaniding 3,5-diglucoside, and delphinidin 3,5-diglucoside. Although these anthocyanins have been characterized in both the pomegranate juice and the extract, these lower molecular weight polyphenols comprise a higher proportion of the total polyphenol content in pomegranate juice (approximately 50%) than in the extract.

Accordingly, methods are provided for producing an extract containing phytochemicals from pomegranate solids. The extract produced from the methods disclosed herein differ from the commercially-available pomegranate juice in that the extract is substantially derived from the pomegranate solids, whereas pomegranate juice is substantially derived from the sweet, fleshy arils that surround the pomegranate seed. The extract is characterized as containing polyphenols and, particularly, high molecular weight polyphenols, such as punicalagin.

In one preferred embodiment, the method comprises providing anyone or a combination of pomegranate solids selected from the group consisting of the pericarp, inner membrane and seeds and creating a mixture comprising the pomegranate solids in an aqueous solution. In a preferred embodiment, the mixture of the pomegranate solids is created by adding water in an amount that is about 20-80% w/v, and more preferably about 50% w/v, of the pomegranate solids. The mixture is preferably crushed or milled to create a rough grind of pomegranate solids dispersed in the aqueous solution.

The mixture is then heated to a temperature of about 60° F. to 210° F., preferably of about 85° F. to 185° F. and optimally of about 110° F. to 160° F. The temperature to which the mixture is heated depends upon the selection of enzymes, or combination of enzymes, that is added to the mixture. Preferably, the mixture is heated to a temperature that permits the maximum catalysis of the enzyme or combination of enzymes.

Alternatively, enzymes may be added before the mixture is heated. Thus, the order of the steps of heating the mixture and adding the enzymes is not critical, so long as the mixture is heated to a temperature that permits the enzymes to at least partially degrade the pomegranate solids and liberate phytochemicals from the plant tissues and/or cells. Once liberated, the phytochemicals may react and/or polymerize to create new phytochemical compounds or reaction products.

Enzymes suitable for use in accordance with this embodiment include those which are capable of at least partially degrading the plant tissue or cells to liberate the phytochemicals from the pomegranate solids. Such enzymes include anyone or a combination of pectinase, cellulase, hemicellulase, amylase, arabanase, and other hydrolyzing enzymes, to name a few. The enzymes added to the mixture may be naturally-occurring or synthetic. They may be derived from any one or a combination of sources, such as animal, plant, fungal, and bacterial sources. The amount of the enzyme or combination of enzymes added to the mixture depends on the temperature of the mixture and the amount of pomegranate solids present in the mixture.

After enzymes are added, the mixture is maintained at a temperature for a time sufficient to allow at least partial degradation of the pomegranate solids. The temperature and length of time required depends on the type of enzymes added to the mixture, the rate of enzyme catalysis and the amount of the pomegranate solids contained in the mixture.

Thus, in one preferred embodiment, a combination of pectinase, cellulase and hemicellulase enzymes are added to the mixture, which is heated to a temperature of about 60° F. to 210° F., preferably about 110° F. to 160° F., and optimally of about 120° F. The mixture is maintained at these temperatures, preferably with agitation or stirring, for about 45-195 minutes, preferably for about 45-75 minutes, and optimally for about 60 minutes.

After the enzymes have at least partially degraded the pomegranate solids, the residual insoluble solid materials are removed from the mixture. Optionally, a clarification agent, such as bentonite, may be added before the step of removing the residual insoluble materials from the mixture. The removal of residual insoluble materials from the mixture may be accomplished by filtration, centrifugation, chromatographic techniques, and other techniques. Filtration techniques suitable for the practice of the methods disclosed herein include micro-filtration at a molecular weight cut-off of at least 1,000 Da, preferably of about 4,500 Da, and optimally of about 5,500 Da.

The resulting liquid extract may be concentrated in an evaporator under vacuum to about 50-90 Brix (Bx), preferably to about 60-80 Bx, and optimally to about 70 Bx, and pasteurized at a temperature and for a length of time sufficient to kill microorganisms that could cause disease, spoilage or undesired fermentation. In one preferred embodiment, the extract may be pasteurized at a temperature of about 140° F.-280° F., preferably of about 195° F.-240° F., and optimally of about 205° F. The pasteurization may also denature the remaining enzymes that were added to the mixture.

In another preferred embodiment, extracts containing phytochemicals from a pomegranate are provided. Such extracts are characterized by a significantly higher total polyphenol content, particularly of the high molecular weight polyphenol (e.g., punicalagin), than is found in pomegranate juice. Such extracts may be obtained from the methods disclosed herein. In a further preferred embodiment, extracts containing phytochemicals, polyphenols, punicalagin, punicalin, ellagic acid, and metabolite thereof are provided.

In yet another preferred embodiment, food products and beverages are provided comprising the extract containing phytochemicals from a pomegranate. For example, due to the significantly higher total polyphenol content in the extract, an 8 oz sports beverage containing 0.33 oz of the extract may be formulated to deliver the same total polyphenols as a 20 oz single-strength pomegranate juice. The polyphenol content of pomegranate juice is approximately about 1 to 2.25 mg/mL and the amount of polyphenols present in 20 oz of juice is approximately 567 to 1,256 mg. In contrast, the extract may contain a polyphenol content of about 60 to 120 mg/mL, depending on the method employed.' Thus only 0.33 oz of the 70 Bx extract would be needed to provide the equivalent amount of polyphenols in 20 oz of the juice.

In a further preferred embodiment, compositions comprising the extract containing phytochemicals from a pomegranate are provided. The compositions may be formulated in the form of tablets, suspensions, implants, solutions, emulsions, capsules, powders, syrups, liquid compositions, ointments, lotions, creams, pastes, gels, and the like.

The compositions may also be prepared in forms suitable for use as pharmaceutical preparations, nutritional supplements, vitamin supplements, food supplements, and food additives. As such, the compositions may optionally include a suitable carrier or excipient.

Suitable carriers or excipients are inert ingredients and include, by way of example, fillers, e.g. sugars such as lactose, glucose or sucrose, sugar alcohols such as mannitol, sorbitol or xylitol, starch such as wheat, corn or potato starch, modified starch or sodium starch glycolate, lubricants such as talc, magnesium stearate, calcium stearate, colloidal silica or stearic acid, and binders such as polyvinylpyrrolidone, cellulose derivatives, carboxymethyl cellulose, hydroxylpropyl cellulose, hydroxypropylmethyl cellulose, methyl cellulose or gelatin. Conventional procedures for preparing such compositions in appropriate, dosage forms of the extract may be utilized. Such compositions may be administered orally or parenterally employing liquid form preparations containing the extract.

The compositions may be administered orally, in appropriate dosage units of the extract in a pharmaceutically acceptable carrier or excipient. Thus, the compositions may be formulated into solid or liquid preparations, such as capsules, pills, tablets, powders, solutions, suspension, or emulsions and may be prepared according to methods known in the art for the manufacture of such compositions. The solid unit dosage forms may be in form of a hard or soft shelled gelatin capsule containing the extract and a suitable carrier or excipient.

The composition may also be administered parenterally as injectable dosages in a physiologically acceptable carrier. Parenteral administration may be subcutaneous, intravenous, intramuscular, or interperitoneally.

The effective amount of a composition is the amount or dosage unit of the extract sufficient to achieve the intended beneficial health results. Accordingly, the effective amount of the composition to be administered depends on considerations such as the dosage unit employed, the mode of administration, the period of treatment, the age, sex and weight of the person treated and the nature and extent of the condition treated. The effective amount can readily be determined based upon standard techniques known to evaluate whether the intended effect of the composition has been achieved, by standard toxicity tests and by standard pharmacological assays.

In a further preferred embodiment, compositions containing the extract and the pomegranate juice are provided. The combination of the extract and pomegranate juice not only produces a composition having a higher total polyphenol content, as compared to the pomegranate juice alone, but it also provides the broad spectrum of the different polyphenols which predominate the pomegranate juice and extract, for example the lower molecular weight polyphenols (e.g., anthocyanins) which is present in greater quantities in the pomegranate juice and the higher molecular weight polyphenols (e.g., punicalagin, punicalin, ellagic acid glycosides, ellagic acid polyphenols, ellagitannin and other hydrolysable tannins, such as punicacortein A, punicalin, pedunculagin, and gallotanin dimmers and timers).

In yet a further preferred embodiment, methods are provided for ameliorating disease conditions in a subject by administering to the subject an effective amount of the composition suitable for use as a pharmaceutical or nutritional preparation.

Thus, in one preferred embodiment, methods are provided for formulating a composition suitable for use as a pharmaceutical or nutritional preparation for improving the health of a subject comprising obtaining an extract containing phytochemicals from a pomegranate and admixing an effective amount of the extract with a suitable carrier or excipient. In another preferred embodiment, methods are provided for treating a polyphenol-mediated condition in a subject comprising selecting a subject having a polyphenol-mediated condition and administering to the subject an effective amount of the composition comprising the extract.

The composition of the present invention may be used to treat influenza viral infection, since the composition of the present invention has significant antiviral properties as demonstrated by the examples of this application. The composition of the present invention may also be used as a therapeutic composition to treat one or more symptoms of a viral infection, including, but not limited to, sore throat, congestion, laryngitis, mucositis, and/or mucous membrane inflammation by administration to a subject suffering from one or more of these symptoms or ailments.

The composition of the present invention may also be employed to reduce the incidence of contracting an illness. In this application of the composition of the present invention, a safe and effective amount of the composition of the present invention is administered to a mammal or a bird that has been or will be exposed to an illness caused by a microbe, to reduce the incidence of contracting said illness, relative to a mammal or a bird that has been or will be exposed to an illness caused by a microbe to which the composition of the present invention has not been administered.

The composition of the present invention may also be formulated with an acceptable carrier. The acceptable carrier may include, but is not limited to: (a) carbohydrates including sweeteners, fructose, sucrose, sugar, dextrose, starch, lactose, maltose, maltodextrins, corn syrup solids, honey solids, commercial tablet nutritional supplements (b) sugar alcohols including mannitol, sorbitol and xylitol; and (c) various relatively insoluble excipients including dicalcium phosphate, calcium sulfate, calcium carbonate, microcrystalline cellulose and other tableting ingredients.

The composition of the present invention may also be formulated into a nasal aerosol or inhalant composition. Such a composition may be prepared using well-known techniques. For these types of formulations, suitable carriers may include the following ingredients: saline with one or more preservatives, absorption promoters to enhance bioavailability, fluorocarbons, and/or conventional solubilizing or dispersion agents.

For the purpose of the invention, an extract from pomegranate may be an extract from the whole pomegranate fruit or from any constituents of pomegranate fruit. Examples of constituents of pomegranate fruit that may be used to make the extract of the invention include, but are not limited to, juice, seed, and the inner and outer peel of pomegranate fruit. In one embodiment of the invention, the extract is the juice extract of whole pomegranate fruit. In another embodiment of the invention, the extract is from the inner or outer peel of pomegranate fruit. In a further embodiment of the invention, the extract may be a mixture of two or more extracts of the whole pomegranate or any constituents of pomegranate.

In general, any methods that may produce pomegranate juice that naturally occurs in pomegranate may be used. For the purpose of the invention, the juice may be concentrated or diluted from its natural concentration. The juice may also be mixed with extracts of other constituents of pomegranate to vary the composition. Methods of making the extract, including the juice from whole pomegranate fruits are described in U.S. Pat. No. 6,977,089 entitled "METHODS OF USING POMEGRANATE EXTRACTS FOR CAUSING REGRESSION IN LESIONS DUE TO ARTERIOSCLEROSIS" which is incorporated herein by reference in its entirety.

Extracts from the constituents of pomegranate, i.e., seeds or the inner or outer peel, may be made by various methods. For example, the seeds or the inner or outer peel of pomegranate may be diluted in water and the extract may be made by crushing, squeezing, or extensive vortexing. The insoluble materials of the extract may be separated from the soluble supernatant of the extract. In some instances, the supernatant of the extract is used for the purpose of the invention, although any oily, lipidic fraction of the extract may also be used. The extract from constituents of pomegranate may be concentrated or diluted, or mixed with each other or with pomegranate juice extract.

In accordance with one embodiment of the invention, the extract of the present invention may be prepared by a process including the steps of: (a) crushing and squeezing the whole fruits of the pomegranate, including the inner and outer peels and the seeds, to yield a juice component and an insoluble by-product component, and (b) separating the juice component from the insoluble by-product component. The juice component may be used as a juice extract of the invention. The insoluble by-product component may be resuspended in an aqueous medium, such as, but not limited to, water or alcohol, and be further crushed, squeezed, and mixed to yield a soluble portion and an insoluble portion. Then the soluble portion may be separated from the insoluble portion to produce the extract of the constituents of the invention. Alternatively, the soluble portion may be combined with the juice extract to produce the extract of the invention.

In one embodiment of the invention, the whole fruit of the pomegranate may be enzymatically treated to improve extraction and filtration. For example, pectinase may be used to treat the whole fruit to prevent the formation of pectin gels. Other enzymes may also be used as long as they can improve extraction and filtration of the extract of the invention.

The extract of pomegranate used in accordance with one or more embodiments of the invention may be in a liquid or solid form. In accordance with one embodiment of the invention, a solid form of the extract may be made by lyophilizing the liquid extract of the invention. Alternatively, the constituents of the pomegranate, such as seeds, inner or outer peels, or any insoluble portion discussed above, may be processed directly to form the solid form of the extract of the invention. For example, the constituents of the pomegranate may be dried, and processed into powder or pill forms to be used directly as the solid form of the extract of the invention.

Compositions of one or more embodiments of the invention may be a variety of kinds, including, but not limited to, nutritional supplements, pharmaceutical preparations, vitamin supplements, food additives, or foods supplements. Compositions of the invention may be in convenient dosage forms, including, but not limited to, tablets, suspensions, implants, solutions, emulsions, capsules, powders, syrups, liquid compositions, ointments, lotions, creams, pastes, gels, or the like.

Compositions of one or more embodiments of the invention may include a carrier. Depending on the kind of compositions of the invention, a carrier may be a dietary suitable carrier or a pharmaceutically acceptable carrier, as long as it is compatible with the particular kind of compositions of the invention. Examples of a dietary suitable carrier include, but are not limited to, dietary suitable excipients, diluents, and carriers. Examples of a pharmaceutically acceptable carrier include, but are not limited to, biocompatible vehicles, adjuvants, additives, and diluents to achieve a composition usable as a dosage form. As used herein, the terms "pharmaceutically acceptable," "physiologically tolerable," and grammatical variations thereof, as they refer to compositions, carriers, diluents, and reagents, are used interchangeably and represent that the materials are capable of administration to or upon a mammal without the production of undesirable physiological effects.

The compositions of one or more embodiments of the invention may be used alone or in combination with other biologically active ingredients. A composition of embodiments of the invention, alone or in combination with other active ingredients may be administered to a subject in a single dose or multiple doses over a period of time, generally by oral administration. Various administration patterns will be apparent to those skilled in the art. The dosage ranges for the administration of the compositions of the invention are those large enough to produce the desired effect. The dosage should not be so large as to cause any adverse side effects, such as unwanted cross-reactions and the like. Generally, the dosage will vary with the age, weight, sex, condition, and extent of a condition in a subject, and the intended purpose. The dosage can be determined by one of skill in the art without undue experimentation. The dosage can be adjusted in the event of any counter indications, tolerance, or similar conditions. Those of skill in the art can readily evaluate such factors and, based on this information, determine the particular effective concentration of a composition of the invention to be used for an intended purpose.

In one embodiment of the invention, a composition contains the extract of pomegranate in a dosage unit in an amount that contains at least 30 to 10,000 parts per million or 30 to 3,000 mg of polyphenols. For the purpose of the invention, polyphenols are those naturally present in the extract of pomegranate. It should be appreciated that polyphenols are used herein as a measurement marker for the amount of extract used in each dosage unit. Polyphenols are not used herein as being indicative of the only active, ingredients of the extract. It is possible, for example, that other elements of the composition or the synergy of polyphenols and other components of an extract of the invention, are responsible for the activities of the extract.

The term "dosage unit" as used herein refers to physically discrete units suitable as unitary dosages for subjects, each unit containing a predetermined quantity of active material calculated to produce the desired therapeutic effect in association with the required diluent, e.g., a carrier or vehicle. The specifications for the unit dose of this invention are dictated by and are directly dependent on (a) the unique characteristics of the active material and (b) the limitations inherent in the art of compounding such active material for therapeutical use in subjects.

Prophylactic treatment is aimed at a subject that will soon be exposed to a virus or has recently been exposed to a virus. Such prophylactic treatment may be effective either alone, or to augment a vaccine or another anti-viral drug. Prophylactic treatment may also be used against viruses for which there are not yet a vaccine available. In the case of prophylactic treatment, the composition of the invention is administered to a subject that will be exposed to a virus or has recently been exposed to a virus for the purpose of reducing the incidence of active infection by the virus in that subject.

In another aspect, the present invention relates to a method of reducing, treating or preventing of at least one symptom or adverse effect of viral infection by administering, to a subject infected with a virus, a composition of the present invention, including ingredients that can be obtained from pomegranate.

In the method, the subject may be a human, an in vitro cell system, or an animal. Preferably, the subject is a mammal, more preferably, a human. In the method, the virus that may be inhibited by administration of the composition of the present invention includes, among other viruses, rhinoviruses, influenza viruses, West Nile virus, herpes simplex virus, HIV-1, HIV-2, adenovirus, cornavirus, influenza virus, rubella virus, yellow fever virus and respiratory syncytial virus (RSV). In a preferred embodiment, the viruses that may be inhibited by administration of the composition include at least Influenza A/Hong Kong/8/68 (H3N2).

Alternatively, the subject may be a member of the bird (Avian) species, which includes the common commercial poultry birds: turkeys, ducks, geese and chickens, less commonly the ostrich as well as other bird species that are commonly kept as house pets, for example canaries and parrots. The composition may be administered by directly spraying the composition into the nasal passage of the bird or the composition may be administered by creating a mist through which the birds walk. Thus, the composition may be given prophylactically to act in a virucidal or virustatic manner. Alternatively, the composition may be used to reduce the transmissivity of the virus.

The symptoms, caused by a viral infection, that may be treated, reduced, or at least partially prevented by this method of the present invention, may include one or more of headache, joint pain, fever, cough, sneezing, muscle ache, running nose, dry mouth, dizziness, and other symptoms related to viral infection. In birds, these symptoms include a lack of energy, decreased egg production, soft shelled eggs, a swelling of the head, eyelids, etc., nasal discharge, coughing or diarrhea.

The effective amount of the composition will vary depending on such factors as the subject being treated, the particular mode of administration, the activity of the particular active ingredients employed, the age, bodyweight, general health, sex and diet of the subject, time of administration, rate of excretion, the particular combination of ingredients employed, the total content of the main ingredient of the composition, and the severity of the illness or symptom. It is within the skill of the person of ordinary skill in the art to account for these factors.

When the composition is administered as a spray, the amounts each of the active ingredients may be reduced as the spray composition delivers the active ingredients more directly to the location where they are needed, as compared to a lozenge or capsule for example.

The following examples are intended to illustrate, but not to limit, the scope of the invention. Indeed, those of ordinary skill in the art can readily envision and produce further embodiments, based on the teachings herein, without undue experimentation. The scope of invention is to be determined by the claims appended hereto.

EXAMPLE 1

Production of Liquid Extract from Pomegranate Solids

The starting material for the production of the extract is the pomegranate solids, which generally comprise the pericarp, the inner membrane and seeds of the pomegranate. The pomegranate solids were obtained and collected after the primary juice from the arils had been substantially expelled or otherwise removed from the pomegranate by pressing, crushing, or other methods known to the art for extracting pomegranate juice.

The pomegranate solids were then transferred to three Reitz Mills with ⅜-inch screens. The material was milled to a fine puree and heated to approximately 125° F. This step, coupled with the following enzyme addition, assisted in breaking down the colloidal structure of the remaining pomegranate solids, thereby releasing the remaining soluble solids.

The mixture was heated to a temperature of about 125° F. for two hours. Three enzymes were added to the mixture: pectinase (Rohapect® DA6L), cellulase/pectinase (Rohapect® CL), and hemi-cellulase/pectinase (Rohapect® B1L). These enzymes were used to liberate the remaining pomegranate soluble solids, such as sugars, minerals, anthocyanins, and remaining polyphenols.

The mixture was then pumped from the extraction plant to the primary processing plant where it was held in the mash treatment tanks for approximately one hour. After one hour, 50-100 pounds of bentonite in a 125 gallon water slurry, per 8,000 gallons of the mixture, was added for protein removal. The treated mixture was then passed through a Westphalia 755 Decanter for removal of solids. The residual insoluble material was discharged as waste.

The remaining liquid extract was processed in a Schmidt evaporator. In this step, the extract was stripped and rectified. In addition, the liquid extract was pre-concentrated and then pasteurized to 205° F. for 45 seconds. The liquid extract then exited the evaporator and was filtered on Koch Micro-Filtration membranes at a 4,500 Da molecular weight cut-off for liquid extract soluble solids.

The liquid extract then re-entered the evaporator for final concentration. Initial heat on this step was about 185-195° F. At about 70 Bx, the liquid extract was cooled to less than about 45° F. and pumped to the concentrate batching room where it was blended and standardized.

EXAMPLE 2

Comparison of Polyphenol Content in Extracts of Pomegranate Solids and in Pomegranate Juice The concentrations of punicalagin, punicalin, ellagic acid glycosides, and ellagic acid polyphenols in the pomegranate juice and the pomegranate extract were analyzed and compared in a University study.

All samples (50 mL injection volume) were filtered (0.22 mm) and analyzed on a Novapak (Waters Corp.) C-18 column, 150×3.9 mm i.d., 5 mm. The mobile phase, solvent A (2% $CH_3COOH/H_2O$) and solvent B (2% aqueous $CH_3COOH/CH_3OH$) was used under linear gradient conditions starting with 99% solvent A in solvent B to 40% solvent A in solvent B over 40 minutes, hold time, 5 minutes with a flow rate of 1 mL/min. All compounds were detected at 254 nm, and at 378 nm (punicalagins) and 366 (ellagic acid) for quantification. Table 1 shows a side-by-side comparison of the concentration of the polyphenols: punicalagins, punicalin, ellagic acid glycosides, and ellagic acid in the pomegranate extract and the pomegranate juice.

TABLE 1

| Compound Name | Pomegranate Extract Concentration (mg/ml) | Pomegranate Juice Concentration (mg/ml) |
|---|---|---|
| Punicalagin (β isomer) | 4.79 | 0.02 |
| Punicalagin (α isomer) | 21.80 | 0.15 |
| Punicalin | 3.62 | NA |
| Ellagic Acid Glycosides | 19.65 | 0.33 |
| Ellagic Acid | 18 | 0.74 |
| Total | 67.86 | 1.24 |

The pomegranate extract concentration of Table 1 is a polyphenol composition for comprising punicalagin and punicalin, wherein a ratio of punicalagin and punicalin to ellagic acid and ellagic acid glycosides by weight is greater than that found in the pomegranate juice concentration, which is about 1:6. As shown in Table 1, the ratio of punicalagin and punicalin to ellagic acid and ellagic acid glycosides in the pomegranate extract concentration, by weight, is about 3:4. Furthermore, the pomegranate extract concentration of Table 1 has a ratio of punicalagin and punicalin to free ellagic acid of about 3:2.

Although other polyphenols are present in both the pomegranate extract and juice, and this example highlights the unexpected and surprising results in that significantly higher concentrations of polyphenols, particularly of punicalagin, are present in the pomegranate extract than in the pomegranate juice. Table 1 shows a total punicalagin (for both α and β isomers) concentration for the pomegranate extract that is over 26-fold greater than for the pomegranate juice.

EXAMPLE 3

Dosages

While both pomegranate juice and pomegranate solid extract contain various types of the anti-oxidant polyphenols, pomegranate solid extract contains a higher total polyphenol content than the pomegranate juice.

In preferred one embodiment, the composition may be in form of a liquid comprising the extract and pomegranate juice. The total polyphenol content provided by the liquid may be varied by the changing the amount of the pomegranate extract and pomegranate juice contained in the liquid. Table 2 provides examples of the formulations of the liquid composition and the total polyphenol content in the formulations relative to the total polyphenol content in standard pomegranate juice. For example, 8 oz of pomegranate juice by mouth daily, Wonderful variety, is equivalent to 1.5 mmol of total polyphenols per day.

TABLE 2

| Extract/Pomegranate Juice Liquid Composition | Pomegranate Extract (oz) | Pomegranate Juice (oz) |
|---|---|---|
| Formulation 1 2x polyphenol content | 0.13 | 0.8 |
| Formulation 2 3x polyphenol content | 0.26 | 0.8 |
| Formulation 3 4x polyphenol content | 0.39 | 0.8 |
| Formulation 4 5x polyphenol content | 0.52 | 0.8 |

For purposes of this embodiment, the effective amount of the extract that is administered to the patient is at least 0.13 oz (or an equivalent unit or measurement) of the extract administered daily, whether the extract is provided alone or in a composition. The dosage of the extract may be increased by administering a greater dosage or increasing the frequency at which the extract is administered.

In addition to the liquid compositions containing the extract, the extract may also be administered in a solid form, such as pharmaceutical or nutritional preparation that comprises the extract and a pharmaceutically acceptable carrier or excipient.

EXAMPLE 4

A Composition of the Present Invention

Pomegranate juice (PJ) extract (Wonderful variety, POM Wonderful, Los Angeles) was used in studies to confirm the benefits of the treatment set forth herein for influenza. Pomegranates were hand-picked, washed, chilled to 4° C., and stored in tanks The fruit was then crushed, squeezed, and treated enzymatically with pectinase to yield the juice and byproducts, which included the inner and outer peels and the seeds. Pectinase hydrolyzes-1,4-galacturonide bonds in pectin, improving extraction and filtration, and prevents formation of pectin gels. Flavonoids constitute 40% (anthocyanins, catechins, and phenols) of total polyphenols in PJ. More complex polyphenols are also present in the juice. The PJ was filtered, pasteurized, concentrated, and stored at −20° C. until use.

EXAMPLE 5

Treatment of Sore Throat

Each of seven human subjects, suffering from sore throats, ingested one cup of PJ prepared according to Example 1 every four hours.

The human subjects that were treated reported complete relief from the symptoms of their sore throats after ingesting from 1 to 6 cups of PJ. It was also found that each cup of PJ can provide relief from a sore throat for up to 6 hours.

Transmission of cold/flu virus is from person to person usually by personal contact by shaking hands and wipe nose or rub eyes or getting sneeze on and the like.

Mechanism of infection: Upon entry through the nose and the eyes, the virus enters the cells lining the nasopharynx (the area of the upper throat that lies behind the nose) and multiples rapidly. Once viruses reach a high concentration cold/flu symptoms (related to inflammation) rapidly appear.

The nasopharynx is area typically for build high concentration of viruses needed to cause cold or flu symptoms. This build-up of viral concentration is because they are either: (1) trapped by the mucus membranes, which is a natural defense mechanism and/or (2) the viruses concentrate on the outer part of the membranes, where they are less exposed to normal body temperature (since they cannot survive elevated temperatures such as body temperature). The cold/flu viruses are vulnerable on the top of nasopharynx membranes on the upper throat.

Human subjects infected with cold/flu virus not showing symptoms are selected in this study. It is desirable keep the virus concentrations low in the upper throat/nasopharynx during the first few days of infection. This prevents the body's defense mechanism, e.g. sneezing, runny nose, fever, malaise and cough, from turning on as the symptoms may confound the study.

The oral consumption of PJ can strongly inhibit the viruses on the nasopharynx since it coats the lining of the throat/nasopharynx with PJ. The varying amount of PJ used to inhibit viral replication on both surface and inner layers of the cells are shown in FIG. 1.

It should be noted that the concentration of polyphenols in PJ is over 100 times more concentrated than in the diluted PJ as indicated in the FIG. 1. This high concentrated source of polyphenols in PJ can immediately inhibit viral replication, protein transport systems, and residual polyphenols are expected to remain for some period in on the cell surface or mucosal layer surrounding the throat/nasopharynx cells. So PJ is used to treat the nasopharynx which disrupt viral replication and control cold/flu symptom, typically when caught in time before viral levels get too high.

Conclusion: Daily or multi-times per day consumption of PJ may help keep viral concentrations at levels below threshold for symptoms. This study indicates prevention during the first 1-2 day of exposure.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method of treating a viral infection due to influenza in a subject to alleviate one or more symptoms, the method comprising:
    selecting a subject having a viral infection from influenza, and
    administering to said subject an effective amount of a polyphenol composition extracted from pomegranate solids, wherein said polyphenol composition comprises punicalagin, punicalin, ellagic acid and ellagic acid glycosides,
    wherein a ratio of punicalagin and punicalin to ellagic acid and ellagic acid glycosides in said polyphenol composition by weight is greater than 1:6.

2. The method of claim 1, wherein said one or more pomegranate solids comprises at least one of a pericarp, an inner membrane, arils and seeds of one or more pomegranates.

3. The method of claim 1, wherein said ratio of punicalagin and punicalin to ellagic acid and ellagic acid glycosides by weight is about 3:4.

4. The method of claim 1, wherein a ratio of punicalagin and punicalin to free ellagic acid in said polyphenol composition by weight is about 3:2.

5. The method of claim 1, wherein said polyphenol composition is administered in the form of a pharmaceutical preparation.

6. The method of claim 1, wherein said polyphenol composition is administered in the form of a beverage.

7. The method of claim 1, wherein said polyphenol composition is in a form selected from the group consisting of tablets, suspensions, implants, solutions, emulsions, capsules, powders, syrups, liquid compositions, ointments, lotions, creams, pastes and gels.

8. The method of claim 1, wherein said polyphenol composition is produced from a process comprising:
    providing said pomegranate solids comprising of a pericarp, inner membrane and seeds;
    creating a mixture comprising said pomegranate solids in an aqueous solution;
    heating said mixture to a temperature that permits enzyme catalysis of said pomegranate solids;
    adding hydrolyzing enzymes to said mixture in an amount sufficient to at least partially degrade said one or more pomegranate solids; and
    removing residual insoluble solid materials from said mixture to provide said composition.

9. A method for treating at least one symptom of a viral infection from influenza, said method of treatment comprising:
    administering to a subject with a least one symptom of a viral infection from influenza an effective dosage unit of a polyphenol composition comprising pomegranate extract, whereby said pomegranate extract comprises polyphenols and is produced by a process comprising:
        providing pomegranate solids comprising a pericarp, inner membrane and seeds;
        creating a mixture comprising said pomegranate solids in an aqueous solution;
        heating said mixture to a temperature that permits enzyme catalysis of said pomegranate solids; and
        removing residual insoluble solid materials from said mixture to provide said pomegranate extract.

10. The method of claim 9, wherein said symptoms comprise at least one symptom selected from the group consisting of sore throat, congestion, laryngitis, mucositis, and mucous membrane inflammation.

11. The method of claim 9, wherein said effective dosage unit comprises a total polyphenol content greater than a polyphenol content of one cup of pomegranate juice substantially extracted from pomegranate arils.

12. The method of claim 9, wherein said polyphenol composition comprises punicalagin, punicalin, ellagic acid and ellagic acid glycosides in a ratio of said punicalagin and said punicalin to said ellagic acid and said ellagic acid glycosides by weight of about 3:4.

13. The method of claim 9, wherein said polyphenol composition comprises punicalagin, punicalin, ellagic acid and ellagic acid glycosides in a ratio of said punicalagin and said punicalin to said ellagic acid by weight of about 3:2.

14. The method of claim 9, wherein said polyphenol composition is administered in the form of a beverage.

15. The method of claim 9, wherein said polyphenol composition is in a form selected from the group consisting of tablets, suspensions, implants, solutions, emulsions, capsules, powders, syrups, liquid compositions, ointments, lotions, creams, pastes and gels.

* * * * *